United States Patent
Ogiba

Patent Number: 5,323,493
Date of Patent: Jun. 28, 1994

[54] BICYCLIST AIR DEFLECTOR APPARATUS

[76] Inventor: Frank M. Ogiba, 51 Rte. 206, Somerville, N.J. 08876

[21] Appl. No.: 36,550

[22] Filed: Mar. 24, 1993

[51] Int. Cl.⁵ .................. A42B 3/04; A42B 3/16
[52] U.S. Cl. ........................... 2/422; 2/423; 2/10; 2/184.5
[58] Field of Search ............ 2/422, 423, 425, 181, 2/184.5, 205, 209, 185 R, 199, 10, 11, 15; 351/158

[56] References Cited

U.S. PATENT DOCUMENTS

| 830,439 | 9/1906 | James | 2/423 |
|---|---|---|---|
| 2,532,852 | 12/1950 | Oaks | 2/423 |
| 3,856,007 | 12/1974 | Leight | 2/423 |
| 4,633,530 | 1/1987 | Satterfield | 2/423 |
| 4,670,911 | 6/1987 | Dunford | 2/209 |
| 4,796,307 | 1/1989 | Vantine | 2/209 |
| 4,944,361 | 7/1990 | Lindgren et al. | 2/423 |
| 4,995,117 | 2/1991 | Mirage | 2/422 |
| 5,044,014 | 9/1991 | Cornale et al. | 2/209 |

*Primary Examiner*—Clifford D. Crowder
*Assistant Examiner*—Michael A. Neas
*Attorney, Agent, or Firm*—E. Michael Combs

[57] ABSTRACT

A helmet includes a band member mounted integrally to the helmet, with the band member having first and second end portions extending below the helmet, with each end portion including a generally U-shaped deflector structure arranged for positioning in adjacency relative to each ear of an individual bicyclist.

3 Claims, 4 Drawing Sheets

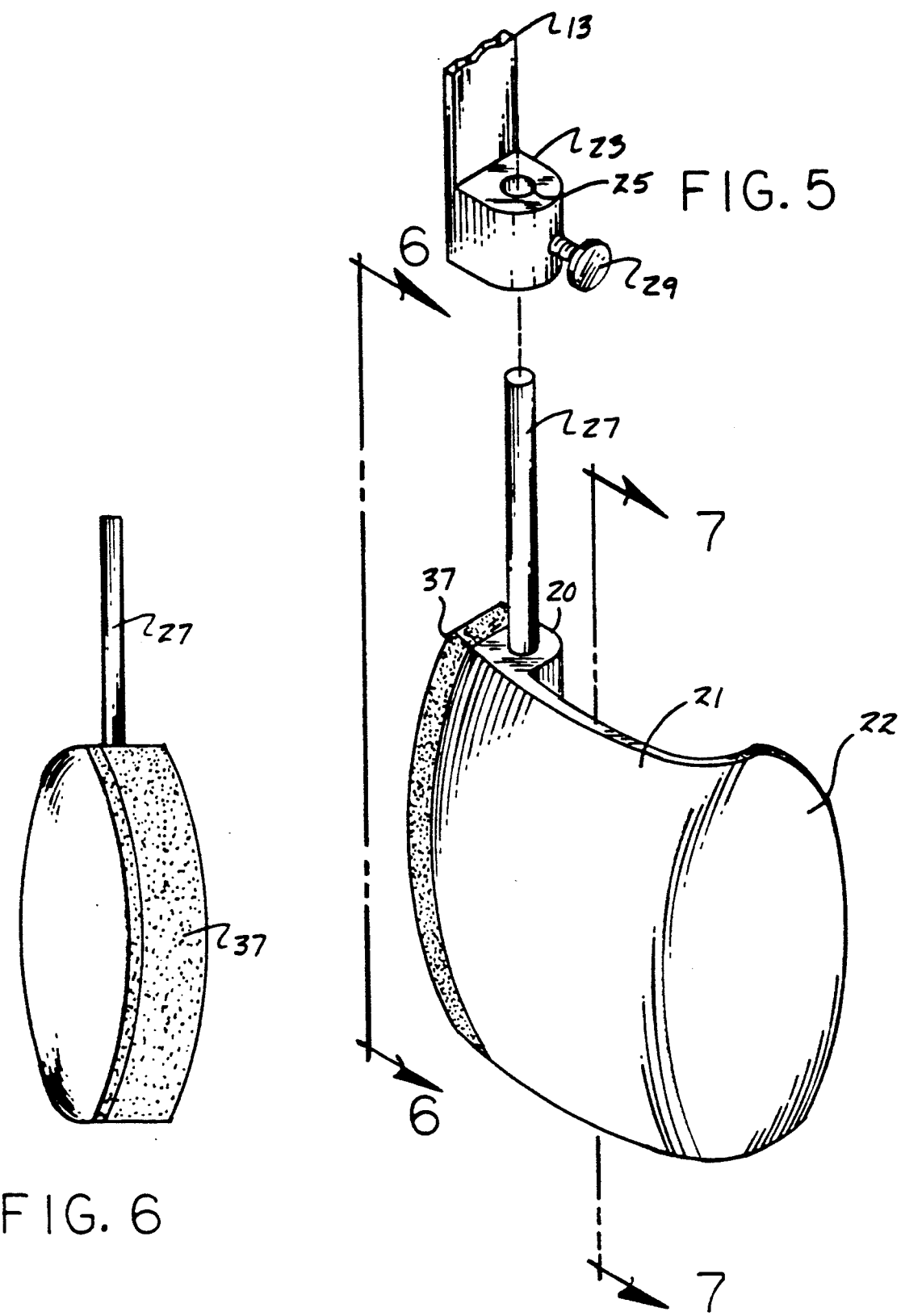

BICYCLIST AIR DEFLECTOR APPARATUS

BACKGROUND OF THE INVENTION

1. Field of the Invention

The field of invention relates to bicycle apparatus, and more particularly pertains to a new and improved bicyclist air deflector apparatus wherein the same is arranged to position an air deflector structure forwardly of each individual's ear during a bicycling procedure.

2. Description of the Prior Art

Ear muff type structure employed for typical usage is cumbersome and awkward in use in a bicycling procedure, wherein as bicycle helmets are typically of a close fitting interrelationship to an individual's head, the ear muff structure is not arranged for ease of fitting relative to an interior surface of the helmet structure. By contrast, the instant invention sets forth an integral structure mounted within the helmet having projecting resilient tabs that position deflector structure forwardly of each individual's ear and in this respect, the present invention substantially fulfills this need.

SUMMARY OF THE INVENTION

In view of the foregoing disadvantages inherent in the known types of bicycle apparatus now present in the prior art, the present invention provides a bicyclist air deflector apparatus wherein the same is arranged to position a plurality of U-shaped deflectors forwardly of each individual's ear. As such, the general purpose of the present invention, which will be described subsequently in greater detail, is to provide a new and improved bicyclist air deflector apparatus which has all the advantages of the prior art ear muff structure and none of the disadvantages.

To attain this, the present invention provides a helmet including a band member mounted integrally to the helmet, with the band member having first and second end portions extending below the helmet, with each end portion including a generally U-shaped deflector structure arranged for positioning in adjacency to each ear of an individual bicyclist.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved bicyclist air deflector apparatus which has all the advantages of the prior art ear muff structure and none of the disadvantages.

It is another object of the present invention to provide a new and improved bicyclist air deflector apparatus which may be easily and efficiently manufactured and marketed.

It is a further object of the present invention to provide a new and improved bicyclist air deflector apparatus which is of a durable and reliable construction.

An even further object of the present invention is to provide a new and improved bicyclist air deflector apparatus which is susceptible of a low cost of manufacture with regard to both materials and labor, and which accordingly is then susceptible of low prices of sale to the consuming public, thereby making such bicyclist air deflector apparatus economically available to the buying public.

Still yet another object of the present invention is to provide a new and improved bicyclist air deflector apparatus which provides in the apparatuses and methods of the prior art some of the advantages thereof, while simultaneously overcoming some of the disadvantages normally associated therewith.

These together with other objects of the invention, along with various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 5 is an isometric illustration of a modified mounting of the deflector structure relative to the band structure.

FIG. 6 is an orthographic view, taken along the lines 6—6 of FIG. 5 in the direction indicated by the arrows.

DESCRIPTION OF THE PREFERRED EMBODIMENT

Figure 1:
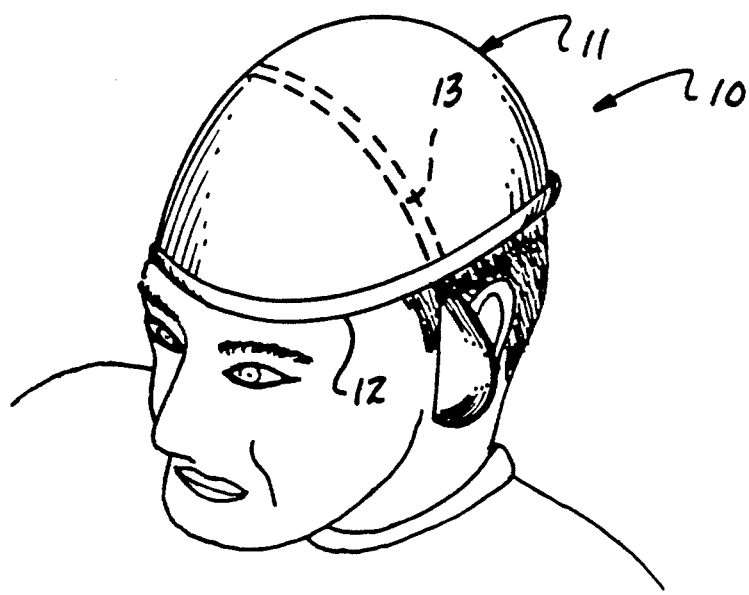
FIG. 1 is an isometric illustration of the invention.
Figure 2:
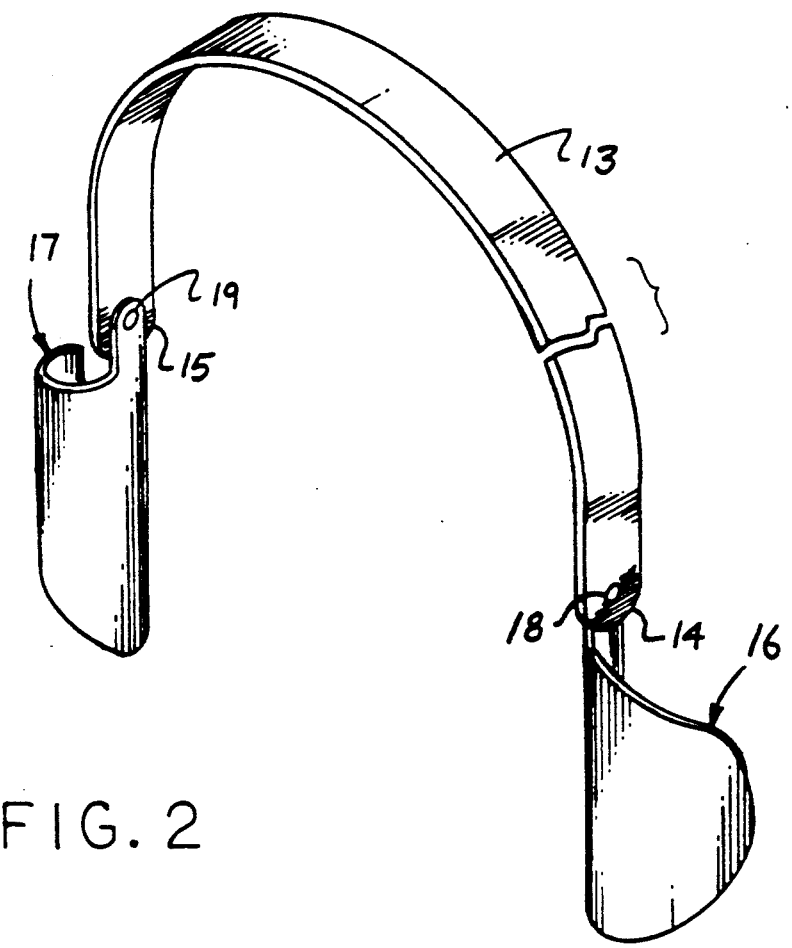
FIG. 2 is an isometric illustration of the band structure indicated in a separated orientation relative to an associated helmet.
Figure 3:
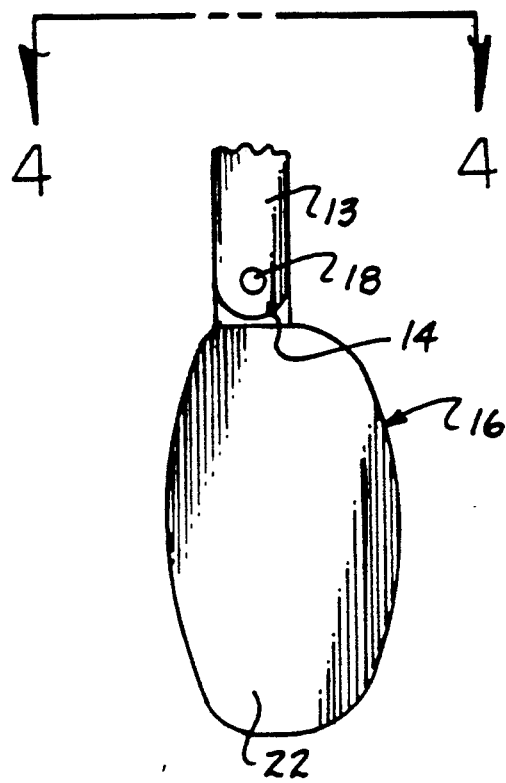
FIG. 3 is an orthographic end view of the deflection structure.
Figure 4:
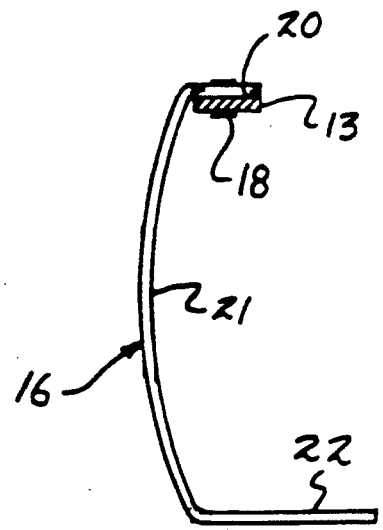
FIG. 4 is an orthographic view, taken along the lines 4—4 of FIG. 3 in the direction indicated by the arrows.

With reference now to the drawings, and in particular to FIGS. 1 to 8 thereof, a new and improved bicyclist air deflector apparatus embodying the principles and concepts of the present invention and generally designated by the reference numeral 10 will be described.

More specifically, the bicyclist air deflector apparatus 10 of the instant invention essentially comprises a helmet 11 having an annular periphery 12, with a resilient band 13 mounted within the helmet 11 extending through the helmet, having band first and second ends 14 and 15 respectively extending orthogonally below the annular periphery 12. Respective first and second axles 18 and 19 are orthogonally directed through the band 13 in adjacency through the first and second ends 14 and 15, having respective first and second U-shaped deflectors 16 and 17 mounted to the respective first and second axles 18 and 19. Each deflector of the first and second deflectors 16 and 17 includes a first plate 20 arranged in a mounted oriented relative to an associated axle, with a second arcuate plate 21 extending from the first plate 20, and a third plate 22 extending from the second arcuate plate 21, wherein the first and second plates 20 and 22 are arranged in a generally facing relationship relative to one another to define a U-shaped configuration of each deflector structure. In this manner, as illustrated in FIG. 1, the apparatus is mounted to an individual's head, wherein each respective deflector is positioned forwardly of the individual's ear for deflection of air about the ear to afford protection relative to the individual's ear subject to wind and depressed temperatures and the like.

The FIGS. 5 and 6 indicate that each of the first and second ends 14 and 15 mounts respective first and second mounting bosses 23 and 24 integrally thereto, with each of the respective first and second mounting bosses 23 and 24 having respective first and second boss bores 25 and 26 directed therethrough, with the boss bores 25 and 26 received within respective first and second shafts 27 and 28 in a complementary relationship, with the first and second fasteners 29 and 30 respectively orthogonally intersecting the respective first and second boss bores 25 and 26 to provide for longitudinal adjustment of the respective first and second deflectors 16 and 17. Further, the first plates 20 and respective first and second deflectors 16 and 17 mount respective first and second resilient pads 37 and 38 thereon, with the first and second resilient pads 37 and 38 (see FIG. 8) arranged in a facing relationship relative to one another from the opposed first and second ends 13 and 14. The first and second resilient pads 37 and 38 provide for enhanced sealing of the deflectors relative to the individual's head, as well as associating comfort in use of the organization.

Figure 8:
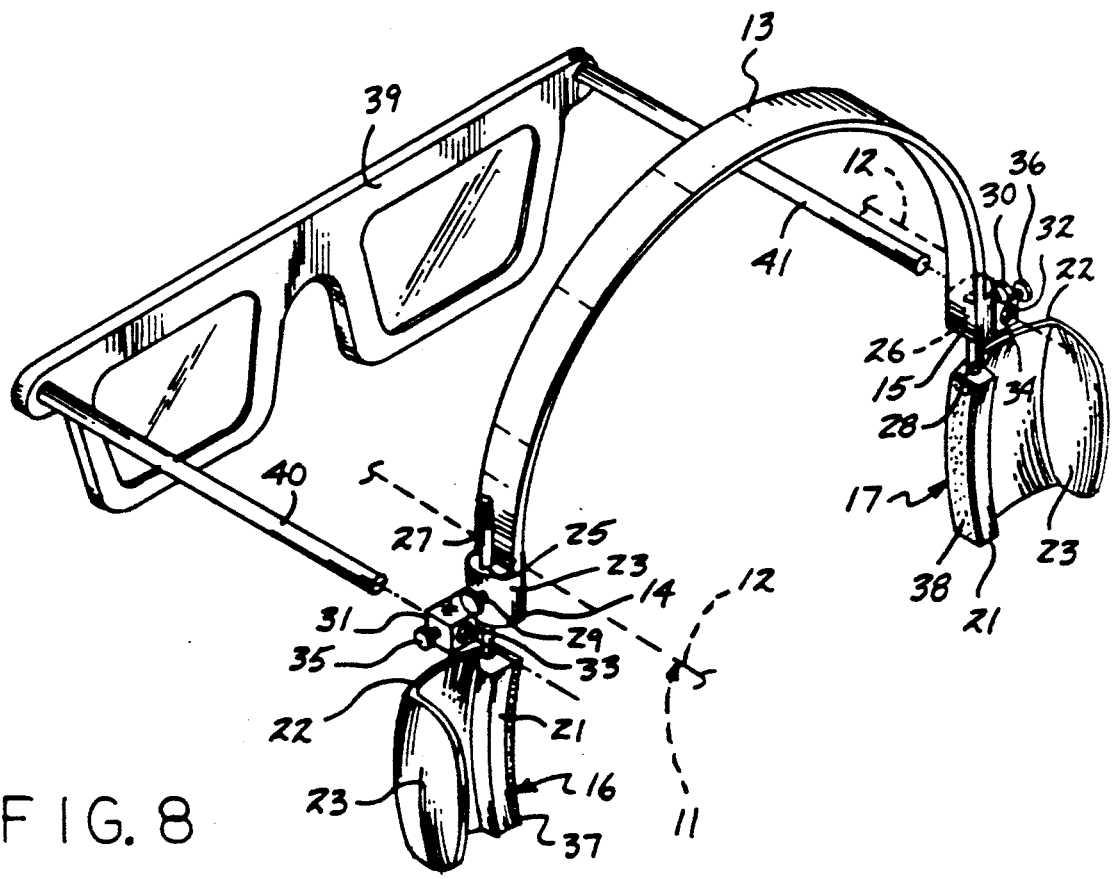
FIG. 8 is an isometric illustration of the invention employing optional mounting of eyeglass members.

FIG. 8 further indicates the use of respective third and fourth bosses 31 and 32 integrally mounted adjacent the first and second ends 13 and 14, with the third and fourth bosses 31 and 32 having respective third and fourth boss bores 33 and 34 directed respectively therethrough, with the third and fourth boss bores 33 and 34 orthogonally oriented relative to the respective first and second boss bores 25 and 26. Third and fourth fasteners 35 and 36 directed respectively through the third and fourth bosses 31 and 32 intersecting the respective third and fourth boss bores 33 and 34 are arranged to secure respective first and second eyeglass rods 40 and 41 of respective eyeglass pair 39. In this manner, the eyeglass pair 39 may be provided for enhanced vision, as well as affording protection to the individual's eyes during a bicycling procedure.

Figure 7:
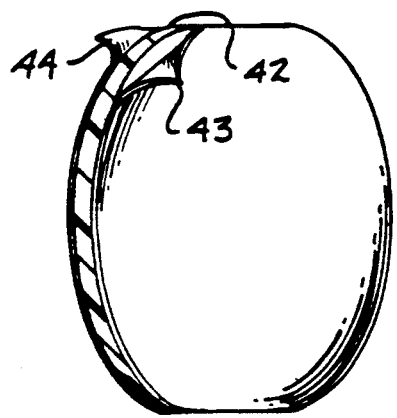
FIG. 7 is an orthographic view, taken along the lines 7—7 of FIG. 5 in the direction indicated by the arrows.

It should be further noted that each of the deflectors, as indicated in FIG. 7, includes a central resilient body 42 having inner and outer fluid impermeable layers 43 and 44 respectively for enhanced weather proofing of the structure during use.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A bicyclist air deflector apparatus, comprising,
   a helmet, the helmet including an annular periphery, and
   a band mounted within the helmet, the band having a first end spaced from a second end, and the first end and the second end project from the annular periphery, and the first end and the second end are arranged in a spaced facing relationship relative to one another, the first end mounting a first U-shaped deflector, and the second end mounting a second U-shaped deflector, wherein the first U-shaped deflector and the second U-shaped deflector are mounted in a mirror image relationship relative to one another, and
   each of the first U-shaped deflector and the second U-shaped deflector include a first plate mounted to the band, the first plate having a second arcuate plate extending from the first plate, and each second arcuate plate including a third plate extending from the second arcuate plate, wherein the first plate and the third plate are arranged in a spaced facing relationship relative to one another, and the first end includes a first mounting boss, the second end includes a second mounting boss, the first mounting boss having a first boss bore, the second mounting boss having a second boss bore, the first U-shaped deflector having a first shaft, the second U-shaped deflector having a second shaft, with the first boss bore receiving the first shaft and the second boss bore receiving the second shaft, wherein the first shaft and the second shaft are arranged in a parallel relationship, and a first fastener directed into the first mounting boss in communication with the first shaft, and a second fastener directed into the second mounting boss in communication with the second shaft permitting the first shaft and the second shaft for adjustable displacement within the respective first mounting boss and the second mounting boss.

2. An apparatus as set forth in claim 1 including a third boss mounted to the band adjacent the first end, and a fourth boss mounted to the band adjacent the second end, with the third boss including a third boss bore, the fourth boss includes a fourth boss bore, the third boss bore and the fourth boss bore arranged in a parallel relationship and orthogonally oriented relative to the first boss bore and the second boss bore, and an eyeglass pair, the eyeglass pair including a first rod and a second rod, wherein the first rod is slidably received through the third boss bore, the second rod is slidably received through the fourth boss bore, wherein the third fastener is directed into the third boss in communication with the first rod, and the fourth fastener directed through the fourth boss in communication with the second rod.

3. An apparatus as set forth in claim 2 wherein the first U-shaped deflector and the second U-shaped deflector each include a central resilient body, having an inner fluid impermeable layer and an outer fluid impermeable layer.

* * * * *